(12) United States Patent
Crawford, Sr. et al.

(10) Patent No.: US 11,214,722 B2
(45) Date of Patent: Jan. 4, 2022

(54) SYSTEMS AND METHODS FOR MOLECULE DISPENSING

(71) Applicant: Vapor Technologies LLC, Platte City, MO (US)

(72) Inventors: John D. Crawford, Sr., Platte City, MO (US); John D. Crawford, Jr., Platte City, MO (US); David G. Fulk, Platte City, MO (US)

(73) Assignee: Vapor Technologies LLC, Platte City, MO (US)

( * ) Notice: Subject to any disclaimer, the term of this patent is extended or adjusted under 35 U.S.C. 154(b) by 203 days.

(21) Appl. No.: 16/537,166

(22) Filed: Aug. 9, 2019

(65) Prior Publication Data

US 2020/0048524 A1 Feb. 13, 2020

Related U.S. Application Data

(60) Provisional application No. 62/717,867, filed on Aug. 12, 2018.

(51) Int. Cl.
| | |
|---|---|
| *A61L 9/03* | (2006.01) |
| *C09K 5/18* | (2006.01) |
| *A01M 31/00* | (2006.01) |
| *A01M 29/12* | (2011.01) |
| *A01M 25/00* | (2006.01) |
| *A01M 1/20* | (2006.01) |
| *A01M 1/02* | (2006.01) |

(52) U.S. Cl.
CPC ............... *C09K 5/18* (2013.01); *A01M 1/023* (2013.01); *A01M 1/2061* (2013.01); *A01M 25/006* (2013.01); *A01M 29/12* (2013.01); *A01M 31/008* (2013.01); *A61L 9/03* (2013.01); *A61L 2209/133* (2013.01)

(58) Field of Classification Search
CPC ....... C09K 5/18; A01M 1/023; A01M 1/2061; A01M 29/12; A01M 31/008; A61L 9/02; A61L 9/03; A61L 2209/133
See application file for complete search history.

(56) References Cited

U.S. PATENT DOCUMENTS

| | | |
|---|---|---|
| 3,046,192 A | 7/1962 | Bilyeu |
| 4,374,571 A | 2/1983 | Hirvela |
| 5,114,625 A | 5/1992 | Gibson |
| 5,220,741 A | 6/1993 | Burgeson |
| 5,307,584 A | 5/1994 | Jarvis |
| 5,429,271 A | 7/1995 | Porter |
| 5,461,814 A | 10/1995 | Reid et al. |
| 5,529,243 A | 6/1996 | Hoyt et al. |

(Continued)

*Primary Examiner* — Timothy C Cleveland
(74) *Attorney, Agent, or Firm* — Lewis Rice LLC

(57) ABSTRACT

A portable, heated scent, odor, and/or molecule dispense system is provided, as well as devices and methods for doing the same. The portable systems and methods to dispense molecules may contain a liquid, gel, solid, foam, or other material-based formulation so as to attract, repel, kill, mask, or otherwise use the molecules. The portable system and methods may include a housing; a molecule holding pad in the housing; a first chemical reaction heat source in the housing; and a second chemical reaction heat source in the housing, wherein the molecule holding pad is arranged between the first chemical reaction heat source and the second chemical reaction heat source, and wherein the first chemical reaction heat source and the second chemical reaction heat source are each reactive to oxygen.

15 Claims, 9 Drawing Sheets

(56) References Cited

U.S. PATENT DOCUMENTS

| | | |
|---|---|---|
| 5,555,663 A | 9/1996 | Brugeson |
| 5,744,106 A | 4/1998 | Eagle |
| 6,050,016 A | 4/2000 | Cox |
| 6,085,989 A | 7/2000 | Cox |
| 6,443,434 B1 | 9/2002 | Prather |
| 7,040,548 B2 | 5/2006 | Rodgers |
| 7,883,677 B2 | 2/2011 | Palozzi |
| 8,496,881 B2 | 7/2013 | Pohl et al. |
| 8,739,455 B2 | 6/2014 | Burgeson |
| 2003/0037476 A1 | 2/2003 | Peavy |
| 2005/0189433 A1 | 9/2005 | Burgeson |
| 2005/0189434 A1 | 9/2005 | Burgeson |
| 2006/0071092 A1 | 4/2006 | Harris, Jr. |
| 2006/0104868 A1 | 5/2006 | Saxon et al. |
| 2013/0015261 A1 | 1/2013 | Scarbrough et al. |

Absorption Core Temperature as a Function of Time at Varying Insulation Thicknesses Absorption Core Temperature as a Function of Time at Varying Insulation Thicknesses

SYSTEMS AND METHODS FOR MOLECULE DISPENSING

CROSS REFERENCE TO RELATED APPLICATION(S)

This application claims the benefit of U.S. Provisional Patent Application Ser. No. 62/717,867, filed Aug. 12, 2018. The entire disclosure of the above document is herein incorporated by reference.

BACKGROUND OF THE INVENTION

1. Field of the Invention

This disclosure relates to the field of portable, heated scent, odor, and/or molecule dispensing systems and methods. More specifically, disclosed herein are embodiments of portable systems and methods to dispense molecules contained within a liquid, gel, solid, foam, or other material-based formulation so as to attract, repel, kill, mask, or otherwise use the molecules.

2. Description of the Related Art

Humans and many animals have a sense of smell. The act of smelling is a form of chemoreception that occurs when odorants, or scents, bind to specific sites within an organism's olfactory receptors, which are typically located in an organism's nasal cavity. The scents themselves are typically chemical compounds (composed of reactive molecules) that may interact with and bind to the organism's olfactory receptors. Such molecules, or scents, are typically introduced to an organism's olfactory receptors via the intake of air around the organism's nasal cavity. For example, a person or a whitetail deer may smell a scent when the molecules of the scent are present around the person or whitetail deer's head and the scent is inhaled through the nose. Scents may enter the air in a number of different ways, for example, some molecules are volatile and readily enter the air. Other molecules may be dispersed into the air using any number of methods, for example, spraying or heating the molecules until the energy from the heat causes the molecules and surrounding air to rise and disperse.

For much of recorded history, humans have endeavored to fill areas with desired scents and other dispensable molecules. People may dispense scents and other molecules in order to provide a desirable smell, to attract animals/insects, to mask an undesirable smell, to kill animals/insects, to react with molecules present in the air, or to affect some other action. For example, some people enjoy filling their home, office, business, bathroom, or other place with scents they find desirable. As another example, hunters have used dispensed natural and man-made scents/molecules in specific areas to affect the behavior of game in that specific area. Such scents may attract desired game or even repel undesired animals or other creatures.

Molecule dispensing may be accomplished in many ways. For example, substances may be presented directly to the area where the molecules are desired to be present. In such a case, a liquid, gel, solid, foam, or other source of molecules may be delivered to the area, and the molecules will naturally disperse due to diffusion. In other situations, some source of energy may be used to increase the dispersion rate. For example, a scent or molecule source may be heated to increase the rate of diffusion (as well as the rate of movement due to convection) of the scent or molecules into the area of interest. Such heating may be accomplished by a device for vaporizing and/or dispensing odorous substances.

The prior art includes basic devices for vaporizing and/or dispensing odorous substances. Most prior art devices require energy, in the form of heat, to operate. Such energy may be background energy present in the area of interest. However, in most examples, the amount of energy required for a satisfactory dispersion will be greater than available in the background of the area of interest. In these cases, sufficient energy may generally be derived through the use of electricity or flammable materials sufficient to promote molecule dispense over a predetermined time span and a sufficient distance.

Most of these devices require sophisticated electronics and controls to ensure user safety and satisfactory performance. Furthermore, most prior art molecule dispense devices contain and require multiple moving components operating within a large system to facilitate the molecule dispense and projection process. Further, these prior art systems typically require relatively expensive components and are generally not disposable. In some instances, such prior systems also included batteries or flammable materials, each of which may present problems due to their instability and the inherent danger of their use. For example, batteries may become ruptured, spilling hazardous contents in the area of the dispense system. Further, flammable materials may ignite in an uncontrolled manner, creating a dangerous fire situation in the area of the dispense system. Further, burning fuel may create odors that are undesirable. In other prior art devices, unnatural gas propellants, such as dimethyl ether or other volatile hydrocarbons, may be found in aerosol liquid sprays. Such propellants and other materials may also create undesirable odors.

Although limited in number, there have been attempts to utilize an exothermic chemical reaction to provide the necessary heat to facilitate and drive molecule dispense. These prior exothermic chemical reaction molecule dispensing systems fail to perform adequately and are primarily only useful in limited temperature range applications. In particular, prior art dispense systems have been inefficient in their ability to transfer heat to the molecules to be dispensed. This is in part due to the limited energy output available from such exothermic reactions. Without focusing and maximizing the efficiency of an exothermic reaction, little energy is available to do work on moving molecules. For example, these prior art systems fail to take advantage of other techniques that may be employed to ensure that most of the heat (including without limitation convention, conduction, and radiation) created by the exothermic reaction is focused on heating molecules and not on heating other matter within the system. Prior art molecule dispense systems that use chemical reactions also fail to properly maintain the chemical reactions. For example, typical prior art systems do not effectively regulate the supply of oxygen to chemical reactions that are based on oxidation. Instead, prior art systems rely on proximity to an exothermic heat source alone, without even attempting to focus or control heat and oxygen paths.

As a result of these and other deficiencies, prior art systems that are portable have failed to produce necessary operating temperatures and failed to operate over necessary time periods. Any failure to produce the necessary temperature and olfactory parameters that mimic natural mammal activities may be undesirable. The inability of prior art products to replicate nature may alarm the desired animals, creating a less effective attractant and poor hunter experiences.

For example, hunters and others with an interest in animals may use wild game lures and attractants. A replication of a deer's naturally occurring olfactory parameters, immediately following excrement and/or urination, communicates safety, confidence, and opportunity to potentially neighboring deer. However, as discussed above, battery or flame operated systems have a number of issues. Further, as discussed, some prior scent systems do away with these energy source and instead use a propellant to disperse scent molecules. However, there are issues with unnatural gas propellants such as dimethyl ether, or other volatile hydrocarbons, typically found in aerosol liquid sprays purveyed in the market today. For example, such propellants create their own, unnatural scents that can be detected by animals.

Replicating nature accurately may produce results not before achieved in molecule dispensing. Whitetail deer, among others, may be able to detect pheromone mixed urine molecules and pass this information directly to their brain—thereby locking what they smell to their long-term memory. Whitetail deer, among others wild game species, may associate and categorize the urination/defecating process as a natural and "good/acceptable" memory, or one without alarm. Urine-based lure products on the market today are unable to incorporate odorless heat and thereby have been unable to replicate the temperature and olfactory parameters immediately after natural mammal excrement or defecation. This inability of portable products today to replicate nature creates whitetail deer alarm and less-than-effective wild game attractant products and consumer experiences.

Stated alternately, whitetail deer, and other wild game animals, may evaluate both opportunity and danger through their superior sense of smell. Superior to even the best tracking canines, deer can discern direction, speed, and intent associated with any scent trail. A hot scent trail, closely replicating a deer's natural temperature profile, communicates safety, confidence, and anticipation as compared to the potential danger of a cold trail comprised of unfamiliar and unnatural odors. The inability of portable products today to replicate nature creates whitetail deer alarm and less-than-effective wild game attractant products and consumer experiences.

SUMMARY OF THE INVENTION

The following is a summary of the invention, which should provide to the reader a basic understanding of some aspects of the invention. This summary is not intended to identify critical elements of the invention or in any way to delineate the scope of the invention. The sole purpose of this summary is to present in simplified text some aspects of the invention as a prelude to the more detailed description presented below.

DETAILED DESCRIPTION OF THE PREFERRED EMBODIMENT(S)

The following detailed description and disclosure illustrates by way of example and not by way of limitation. This description will clearly enable one skilled in the art to make and use the disclosed systems and methods, and describes several embodiments, adaptations, variations, alternatives and uses of the disclosed systems and methods. As various changes could be made in the above constructions without departing from the scope of the disclosures, it is intended that all matters contained in the description or shown in the accompanying drawings shall be interpreted as illustrative and not in a limiting sense.

Generally speaking, described herein, among other things, are portable systems and methods for dispensing molecules contained within a liquid, gel, solid, foam, or other material-based formulation so as to attract, repel, kill, or mask, or otherwise use the molecules. Generally speaking, the systems and methods described herein use an exothermic chemical reaction and a thermally and cost efficient package to increase the diffusion of molecules into the surrounding environment and, in some embodiments, to mimic the scent and temperature profile of natural animals. This exothermic reaction may take different forms. For example, the exothermic reaction may include the oxidation of iron into rust, such in the same way that chemical hand warmers product heat using the oxidation of iron. These exothermic chemical reactions will be discussed in detail later in conjunction with FIGS. 12-14.

Figure 5:
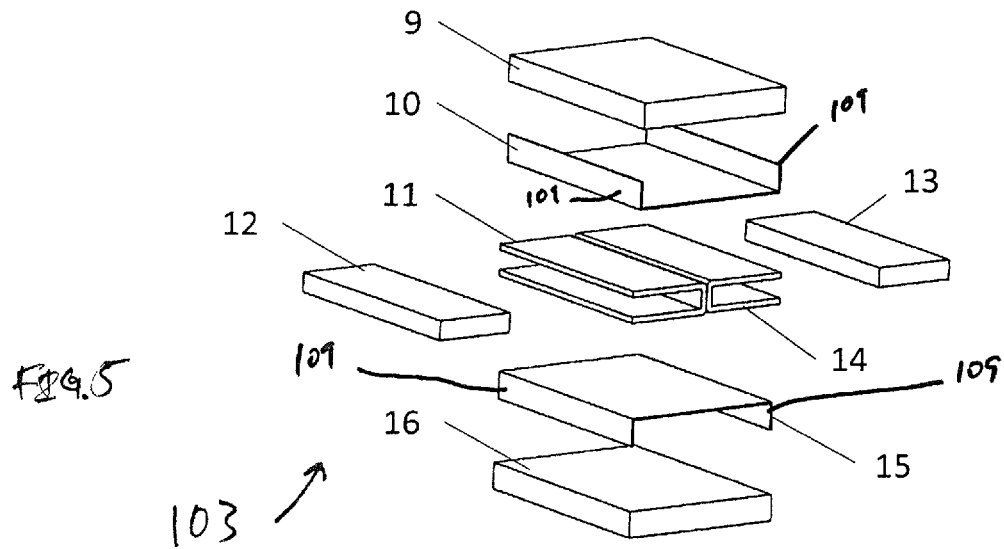
FIG. 5 depicts an embodiment of the internal components that may be placed inside of the housing to facilitate molecule dispense.
Figure 6:
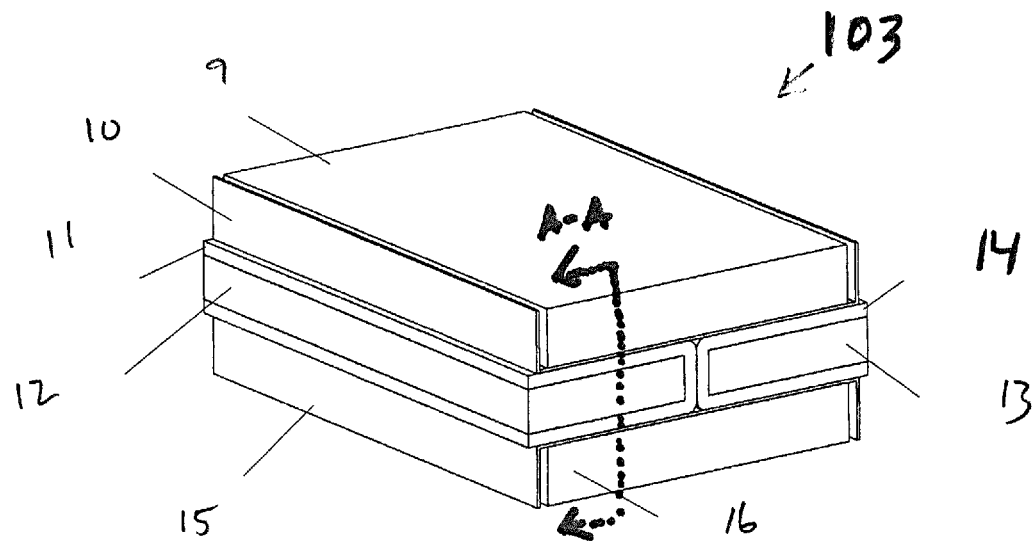
FIG. 6 depicts perspective view of an embodiment of an assembled stack up of the internal components shown in FIG. 5.
Figure 7:
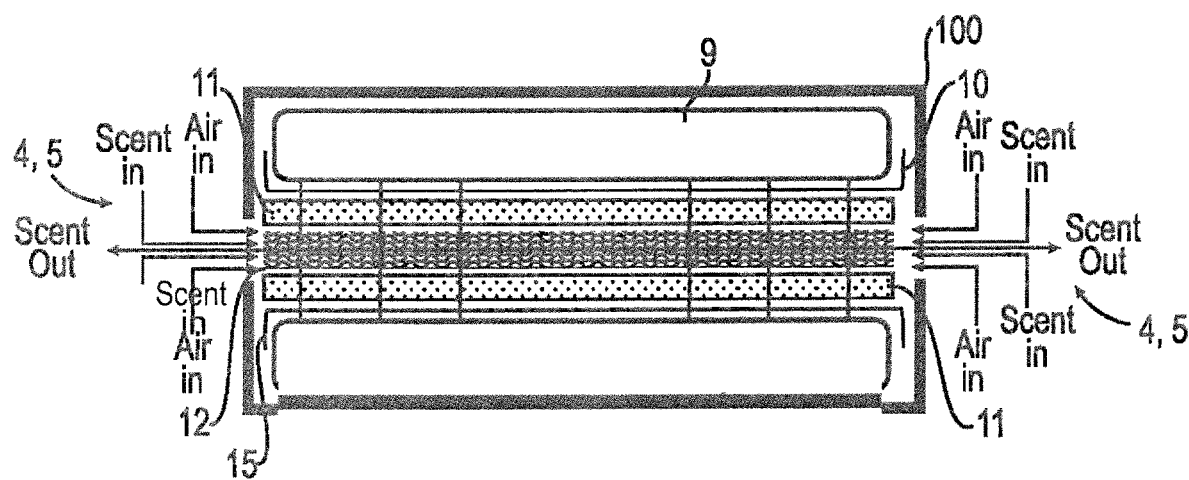
FIG. 7 depicts a cross-section of the embodiment of the internal components shown in FIG. 6 along the A-A line.
Figure 8A:
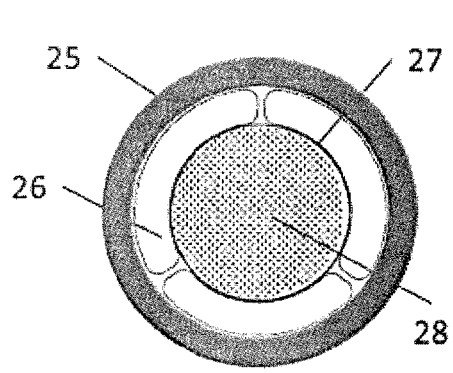
FIGS. 8A and 8B depict cross-sections of embodiments of a molecule dispense system wherein three or four heating elements are used.
Figure 8B:
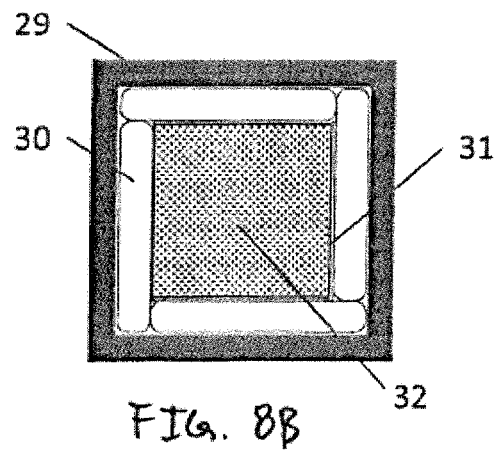

Generally, as shown in the FIGs., a housing (100), described herein, may be used to facilitate molecule dispense. Within the housing (100), an odorless heat may be generated by exothermic chemical reactions, with the housing (100) acting as an insulated, oxygen-regulated environment. This odorless heat may then facilitate molecule dispense when the heat is applied generally across an absorption pad (11, 14; depicted in, e.g., FIGS. 5 and 6) carrying molecules. The absorption pad (11, 14) may be any material that is capable of holding the molecules to be dispense. Further, the absorption pad (11, 14) will typically be capable of allowing the molecules to escape from the absorption pad (11, 14) when exposed to the odorless heat discussed above. The absorption pad (11, 14) may be included in a stack up comprising some separators and some absorption pads. The absorption pad (11, 14) may carry molecules in the form of a liquid, gel, solid, foam, or other form. The dispensed molecules may be transported by a cloud of warm air and water (or other material) vapor, forming an odor trail, which may commonly be referred to as sillage. As water (or other material) vapor is ejected from the housing (100), or otherwise displaced within the housing (100), air surrounding the heated air may start moving around to make space for the heated air and/or to fill the space where the heated air once was, thus generating air flow comprised of the molecules. Stated alternately, without heat, there is negligible opportunity to generate new and useful airflow to propagate and propel sustained molecule dispense.

The molecules may be any number of different scents, formulas, or other substances, and each may have a different use. For example, some water-based scents that may be used with the molecule dispense system include scents that mimic natural animal scents, such as urine, pheromones, or other materials from whitetail deer, mule deer, bear, elk, moose, hog, big horn sheep, bison, caribou, cougar, turkey, wolf, coyote (and other predators), pronghorn, and any other animals or even insects. Further, the molecules for dispensing may be scents of plants, such as sugar beets or acorns. In other embodiments, the molecules may be any substance known to cover or mask odors. In other embodiments, the molecules may be any substance known to deter or repel animals or insects, such as insect repellants known in the art. In other embodiments, the molecules may be any substance capable of being dispensed.

Figure 1:
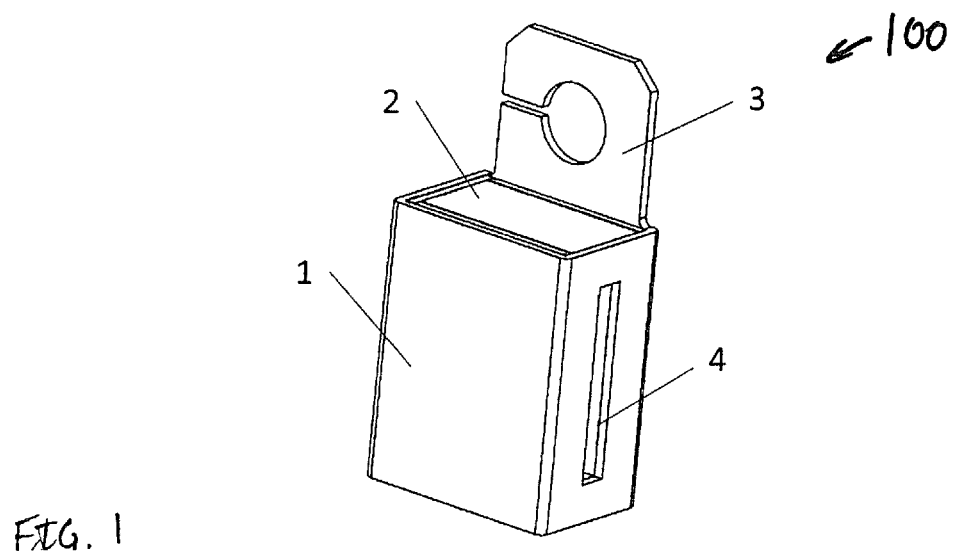
FIG. 1 depicts a perspective view of an embodiment of a molecule dispense system in accordance with this application.
Figure 2:
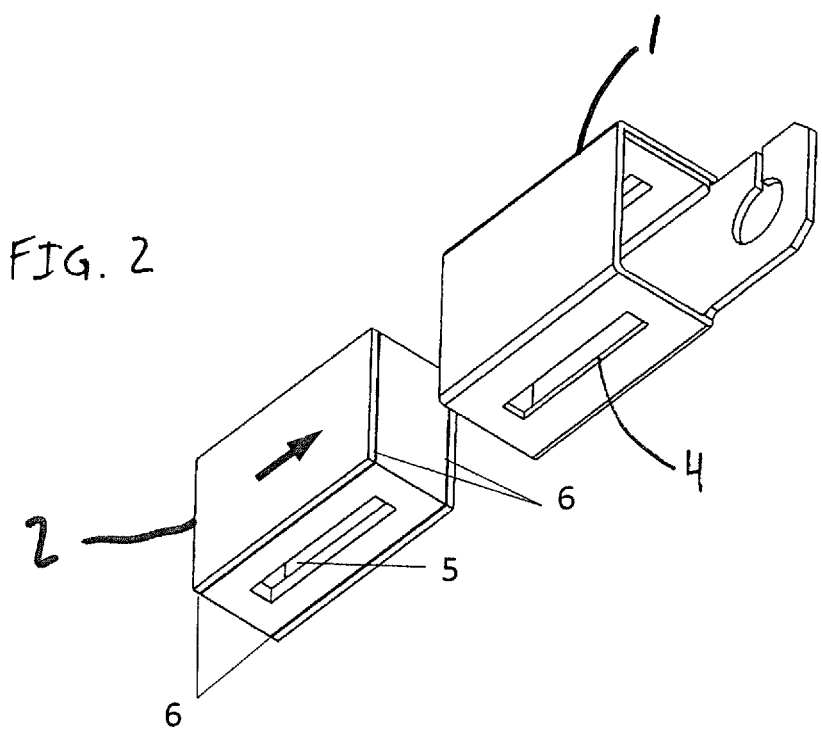
FIG. 2 depicts a perspective view of the embodiment of the molecule dispense system shown in FIG. 1, but provides additional detail regarding the outer sleeve and the internal tray.

FIG. 1 depicts an embodiment of a molecule dispense system in accordance with this application. Specifically, FIG. 1 is a perspective view of a housing (100) for a two heating element (not shown) embodiment of a molecule dispense system. In the depicted embodiment, the housing is comprised of an outer sleeve (1), an internal tray (2), an integral hang hook (3), and primary external air intake/exhaust slot (4). In this embodiment, the outer sleeve (1) and the internal tray (2) comprise a material or combination of materials that provide (a) a sufficient structure for the molecule dispense system and (b) insulation. For example, the outer sleeve (1) and the internal tray (2) may be formed from multiple layers of B-Flute cardboard, which may provide sufficient structural rigidity and resistance to heat flow. The materials' insulative properties may be useful to prevent heat from inefficiently escaping through the housing (100) itself directly into the ambient environment. Further, the outer sleeve (1) or the internal tray (2), or any portion of the housing (100), may be manufactured of an alternate insulatory material. In an embodiment, cardboard is used to make the outer sleeve (1) and the internal tray (2), which material may provide cost-effective insulation. Other materials for the housing (100) may include wood, wool, stone, fiberglass, expanded polystyrene, compression molded or extruded polystyrene, EVA, polyurethane (in foam form or otherwise), other polymer or cellulose based encapsulation products, or any other material. In some embodiments, the materials for the housing (100) may be selected based upon user application, cost, performance, or other requirements.

In the embodiment depicted in FIG. 1, the housing (100) includes an integral hang hook (3). The integral hang hook (3) may be incorporated into the housing (100) to facilitate molecule dispense at an elevated position or otherwise positioned as the user prefers. In some embodiments, the integral hang hook (3) may be removed from the housing (100) at a user's discretion or based on the housing's (100) application. The housing (100) may include perforations in the area of the integral hang hook (3) to facilitate removal of the integral hang hook (3). In the depicted embodiment, the integral hang hook (3) is integrated into the outer sleeve (1). In other embodiments, the integral hang hook (3) may be integrated into the internal tray (2) or into another portion of the housing (100). In other embodiments, the integral hang hook (3) may be integrated into the housing (100) that is formed as a single, integrated piece. In the embodiment depicted in FIG. 1, the integral hang hook (3) is formed of the same material as the outer sleeve (1) and the internal tray (2). In other embodiments, the integral hang hook (3) may be made of a different material than the outer sleeve (1) and/or the internal tray (2).

The housing (100) may include some primary external air intake/exhaust slots (4). As discussed later in conjunction with FIGS. 11-14, in an embodiment, the primary external air intake/exhaust slots (4) allow the exothermic reaction to receive oxygen in a rate-controlled manner. Additionally, the primary external air intake/exhaust slots (4) may create an injection point for facilitating the funneling of the molecule formulation from a storage container (107; depicted in FIG. 10C) onto some absorption pads (11, 14; depicted in, e.g., FIG. 5) that are intended to hold the molecules until the molecules are dispensed in a controlled and relatively consistent manner. There is no limit as to the number of primary air external intake/exhaust slots (4) or their configuration or placement. Further, the primary external air intake/exhaust slots (4) may be of any useful configuration that provides sufficient opening for the dispensed molecules to enter into the ambient environment.

FIG. 2 depicts the embodiment of the molecule dispense system shown in FIG. 1, but provides additional detail regarding the outer sleeve (1) and the internal tray (2). As depicted in the embodiment shown in FIG. 2, a secondary air gap (6) may also be provided. The secondary air gap (6) may provide additional rate-controlled oxygen ingress into the housing (100) while limiting excessive and inefficient heat loss. The secondary air gap (6) may be of any configuration or placement sufficient to promote efficient heat transfer from some heating elements (9, 16) through some separators (10, 15) and the absorption pads (11, 14) and ultimately into the ambient environment.

In an embodiment, the internal tray (2) may fit within the outer sleeve (1). In some cases, the fit between the outer sleeve (1) and the internal tray (2) may be a frictional slip fit that is generally capable of preventing some relative movement between the outer sleeve (1) and the internal tray (2). This fit may allow for the primary external air intake/exhaust slots (4) of the outer sleeve (1) to stay aligned with some primary internal air intake/exhaust slots (5) of the internal tray (2) during use. Further, the resultant multi-layer wall thickness of housing (100), comprised of both the outer sleeve (1) and the internal tray (2), may promote a natural funneling of a molecule formulation onto the absorption pads (11, 14). This arrangement may assist in transmitting molecules to be dispensed from a source, such as a bottle, to the absorption pads (11, 14). In other embodiments, the housing (100) may be constructed of a single piece, wherein some of or all of the features and/or functions of the outer sleeve (1) and the internal tray (2) are combined into a single, integrated structure.

Figure 3:
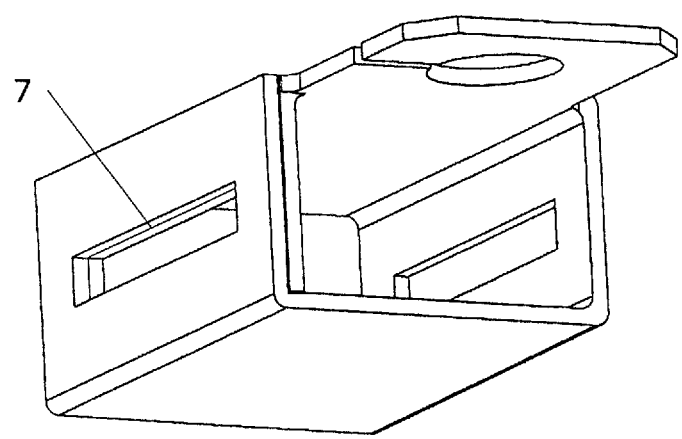
FIG. 3 depicts a perspective view of the outer sleeve of the embodiment of the molecule dispense system of FIG. 1.
Figure 4:
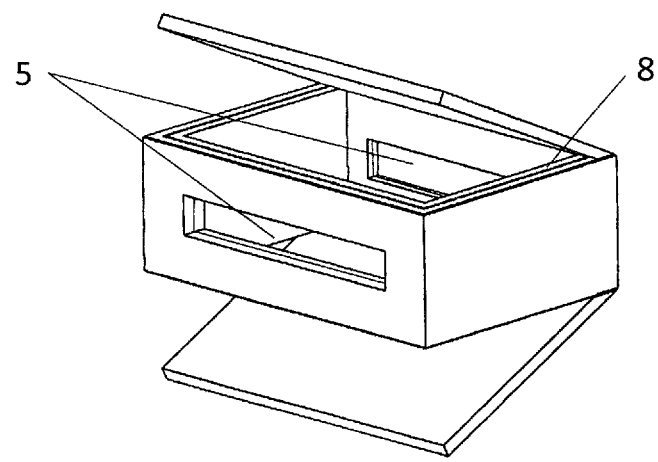
FIG. 4 depicts a perspective view of the internal tray of the embodiment of the molecule dispense system of FIG. 1.

FIG. 3 depicts a perspective view of the outer sleeve (1) of the embodiment of the molecule dispense system of FIG. 1. In this embodiment, the primary external air intake/exhaust slots (4) are aligned with each other on opposite sides of the outer sleeve (1). In some embodiments, this orientation of the primary external air intake/exhaust slots (4) is used to regulate oxygen flow, heat flow, and other variables. Generally, the aligned primary external air intake/exhaust slots (4) orientation may promote saturation of the absorption pads (11, 14) when being filled from a molecule source. In other embodiments, the primary external air intake/exhaust slots (4) may be skewed, or may be formed in non-opposing surfaces of the housing (100). Such a skewed primary external air intake/exhaust slot (4) orientation may be used to shield the internal region of the housing (100) from rain, snow, or other elements capable of diluting the formulation of molecules. Further, although FIG. 3 depicts two primary external air intake/exhaust slots (4), more or less primary external air intake/exhaust slots (4) may be used.

FIG. 4 depicts a perspective view of the internal tray (2) showing a pair of primary internal air intake/exhaust slots (5). As with the primary external air intake/exhaust slots (4), in the depicted embodiment, the primary internal air intake/exhaust slots (5) are aligned with each other on opposite sides of the internal tray (2). In some embodiments, this orientation of the primary internal air intake/exhaust slots (5) is used to regulate oxygen flow, heat flow, and other variables. Generally, the aligned primary internal air intake/exhaust slots (5) orientation may promote saturation of the absorption pads (11, 14) when being filled from a molecule source. In other embodiments, the primary internal air intake/exhaust slots (5) may be skewed or may be formed in non-opposing surfaces of the housing (100). Such a skewed primary internal air intake/exhaust slots (5) orientation may be used to shield the internal region of the housing (100) from rain, snow, or other elements capable of diluting the formulation of molecules. Further, although FIG. 3 depicts two primary internal air intake/exhaust slots (5), more or less primary internal air intake/exhaust slots (5) may be used.

FIG. 3 also depicts an embodiment of the system including an aligned outer layer geometry (7), and FIG. 4 also depicts an embodiment of the system including an aligned inner layer geometry (8). The aligned outer layer geometry (7) indicates that the outer sleeve (1) may comprise at least two layers of material having insulating paths that are aligned along at least one axis. Similarly, the aligned inner layer geometry (8) indicates that the internal tray (2) may comprise at least two layers of material having insulating paths that are aligned along at least one axis. In either case, these aligned orientations may apply to any construction that is substantially aligned. In this application, substantially aligned may include portions that are not aligned. For example, during manufacturing, the portions of the aligned outer layer geometry (7) and/or the aligned inner layer geometry (8) at the corners or edges of the housing (100) may be pinched together, creating misaligned regions local to those corners. Further, in other embodiments, some portions of the aligned outer layer geometry (7) and/or the aligned inner layer geometry (8) may be designed to have portions, such as an area in the middle of a side of the housing (100), that have unaligned layer geometries.

FIG. 5 depicts an embodiment of some internal components (103) that may be placed inside the housing (100) to facilitate molecule dispense. In the embodiment depicted in FIG. 5, the internal components (103) comprise two sets each of heating elements (9, 16), separators (10, 15), absorption pads (11, 14), and air scaffolds (12, 13). Each of these components may be arranged in a symmetrical fashion around the internal absorption pads (11, 14). The components together drive the heat made by the heating elements (9, 16) through the absorption pads (11, 14) and out through the air scaffolds (12, 13). In some embodiments, not all of the above items will be included in the internal components (103). For example, in some embodiments, the internal components (103) may omit the air scaffolds (12, 13). The air scaffolds (12, 13) may be excluded when the housing (100) is used in, for example, a cold working environment because the air scaffolds (12, 13) generally increase heat and molecule dispense from the housing (100), and in such conditions, the air scaffolds (12, 13) may allow heat to escape other than, or faster than, desired through the absorption pads (11, 14). On the other hand, in usage applications where the ambient environment has a temperature greater than 70° F., for example, the air scaffolds (12, 13) may provide additional heat flow and molecule dispense without compromising heat flow efficiency.

As shown in FIGS. 5 and 6, the heating elements (9, 16) may be in direct contact with the separators (10, 15). The separators (10, 15) may incorporate the use of features in the form of "side shields," effectively protecting three surfaces of the heating elements (9, 16) from moisture or other liquid-induced degradation. In other words, the separators (10, 15) may include bent sections at the ends, forming tabs (109, FIG. 5), so that the separators (10, 15) cover the short sides of the heating elements (9, 16). Molecule formulations may be introduced proximate to the heating elements (9, 16), for example, during molecule injection onto the absorption pads (11, 14) by the user or during exposure to rain, sleet, snow, or other weather. The separators (10, 15) are typically comprised of, but not limited to, a polymer film and/or thin poly-coated, cellulose-based materials. In some embodiments, the separators (10, 15) may be breathable, hydrophobic textiles that are capable of retaining and separating water vapor on the side of the heating elements (9, 16). Further, instead of including the tabs (109), the separators (10, 15) may be designed to be relatively planar, but fit within the housing (100) with slight compression before any chemical reaction begins. In the embodiment depicted in FIGS. 5 and 6, the heating element (9) and the separator (10) may be used together to heat one half of the absorption pads (11, 14). In turn, the heating element (16) and the separator (15) may be used together to heat the other half of the absorption pads (11, 14). In the depicted embodiment, the absorption pads (11, 14) are wrapped around three sides of the air scaffolds (12, 13). In other embodiments, the absorption pads (11, 14) may be mated flat against each other and compressed via a mechanical style staple. In other embodiments, the absorption pads (11, 14) may be integrated into a single piece of material.

Each of the heating elements (9, 16), separators (10, 15), absorption pads (11, 14), and air scaffolds (12, 13) may be expanding in their nature. Specifically, each of these may expand when heated. Such expansion may cause compression in of some or all of the expanding heating elements (9, 16), expanding separators (10, 15), expanding absorption pads (11, 14), and expanding air scaffolds (12, 13). Compression may assist with the focusing and driving of heat through the absorption pads (11, 14). Further, compression may increase the efficiency of the process of heating and dispensing the molecules stored within the absorption pads (11, 14).

In an embodiment, the absorption pads (11, 14) may be made of a saturated or unsaturated polyester. Polyesters may be desirable due to their hydrophobic nature and ability to quickly and fully dry. In the case where polyester fibers are used, such fibers may be solid or hollow, or a mixture of both. Such polyester fibers may be woven or unwoven, and may be formed into mats or felts. For example, in an embodiment, the absorption pads (11, 14) may be made of 24-ounce or 32-ounce polyester felt. Generally, denser materials will allow for a slower dispense of molecules than less dense materials, and denser materials will hold less molecules overall than less dense materials. Generally, denser materials are more suitable for colder ambient environments, while less dense materials are more suitable for warmer ambient environments. In other embodiments, the absorption pads (11, 14) may be made of any fibrous material, such as a cotton/polyester blend, which itself may be treated to increase the hydrophobic nature of the materials. In yet other embodiments, the absorption pads (11, 14) may be made of any material capable of retaining and then dispensing molecules.

The air scaffolds (12, 13) may be used to provide an air gap, generally exposing an increased portion of the absorption pads (11, 14) to the ambient environment and the heating elements (16, 17), thereby possibly promoting efficient and increased molecule dispense. Accordingly, the air scaffolds (12, 13) surface may serve as a medium to subject additional molecules to the environment. One such formulation, for example, may be an adhesive residue capable of entrapping and adhering insects, such as mosquitoes, attracted to molecules (such as carbon dioxide) being dispensed from or across the absorption pads (11, 14). The air scaffolds (12, 13) may be fabricated using pieces of single layer cardboard corrugate place back-to-back. In another embodiment, the air scaffolds (12, 13) may be formed from Kraft cardboard that has been folded into an accordion profile. In yet another embodiment, the air scaffolds (12, 13) may be formed from a mesh air filter. The mesh air filter may be a polymer or other material, and may be woven or have another construction. In some embodiments, the air filters may contain open interior channels, which may provide immediate molecule escape across the entire exposed surface area of the relevant absorption pads (11, 14). The mesh itself may be formed to have a pattern much like corrugated cardboard, but with a weaved-mesh portions. The mesh may have a symmetrical or asymmetrical construction.

FIG. 6 depicts perspective view of an embodiment of an assembled stack up of the internal components (103) shown in FIG. 5. This configuration may be contained and oriented within an insulated, oxygen-regulated container such as, but not limited to, the housing (100) having the outer sleeve (1) and the internal tray (2).

FIG. 7 depicts a cross-section of the embodiment of the internal components (103) shown in FIG. 6 along the A-A line, showing some of the internal workings and functionality of that embodiment. FIG. 7 shows some exemplary heat and oxygen circulation paths for the depicted embodiment. Specifically, FIG. 7 shows that heat in the internal components (103) may primarily conduct from the heating elements (9, 16) to the primary external air intake/exhaust slots (4) and the primary internal air intake/exhaust slots (5). Further, FIG. 7 shows a typical air or oxygen cycling process. In particular, air is cycled into the housing (100) via the primary external air intake/exhaust slot (4) and the primary internal air intake/exhaust slot (5). This air is then circulated through the absorption pads (11, 14) and heated by the heating elements (9, 16) using conduction through the separators (10, 15). The heated and molecule-rich air in the absorption pads (11, 14) is then ejected from the housing (100) using convention, completing the air cycle and dispensing the molecules into the ambient environment. At different times, the absorption pads (11, 14) may also be heated by convection from the heating elements (9, 16) by heat air travelling around the separators (10, 15).

FIG. 8A depicts a cross-section of an embodiment wherein three heating elements (26) are used, and FIG. 8B depicts a cross-section of an embodiment wherein four heating elements (26) are used. For the three heating element configuration depicted in FIG. 8A, a circular insulation housing (25) may insulate and control oxygen ingress and egress while limiting heat loss and driving the exothermic reaction heat generated in the heating elements (26) through a circular separator (27) and into a circular absorption pad (28). The heated and molecule-rich air is then ejected from the circular insulation housing (25) at either end of the circular insulation housing's (25) cross-section. Although the depicted embodiment shows a generally circular shape for the various components, other shapes and/or cross-sections may be used. For the four heating element configuration depicted in FIG. 8B, a square insulation housing (29) may insulate and control oxygen ingress and egress while limiting heat loss and driving the exothermic reaction heat generated in the heating elements (30) through a square separator (31) and into a square absorption pad (32). The heated and molecule-rich air is then ejected from the square insulation housing (29) at either end of the square insulation housing's (29) cross-section. Although the depicted embodiment shows a generally square shape for the various components, other shapes and/or cross-sections may be used.

FIGS. 9A-9H depict another embodiment of a housing (100) and related internal components (103) that do not include the air scaffolds (12, 13). Specifically, FIGS. 9A-9H depict an embodiment of a process for assembling the housing (100) and internal components (103). FIG. 9A shows an internal tray (2) being built up with a heating element (16) to form a stack-up that will comprise the internal components (103). FIG. 9B shows the stack-up of FIG. 9A with the addition of a separator (15) placed on top of the heating element (16). FIG. 9C shows the stack-up of FIG. 9B with the addition of a first absorption pad (11) and a second absorption pad (14) placed on top of the separator (15) and the heating element (16). In the depicted embodiment, the first absorption pad (11) is attached to the second absorption pad (14) using a staple. An additional benefit of the staple may be to compress the first absorption pad (11) and the second absorption pad (14), which may improve molecule density and may affect the rate of molecule dispense. Any other manner of connecting the first absorption pad (11) and a second absorption pad (14) may be used, as is known in the art. In other embodiments, the first absorption pad (11) and the second absorption pad (14) may not be attached to each other. In yet other embodiments, the first absorption pad (11) and a second absorption pad (14) may be integrated into a single structure. FIG. 9D shows the stack-up of FIG. 9C with the addition of a separator (10) placed on top of the first absorption pad (11), the second absorption pad (14), the separator (15), and the heating element (16). FIG. 9E shows the stack-up of FIG. 9D with the addition of a heating element (9) placed on top of the separator (10), the first absorption pad (11), the second absorption pad (14), the separator (15), and the heating element (16). This stack-up constitutes the internal components (103) for the depicted embodiment. FIG. 9F depicts the stack-up of internal components (103) and the internal tray (2) being placed on top of an unassembled outer sleeve (1). The outer sleeve (1) includes an integral hang hook (3). Further, in the depicted embodiment, the outer sleeve (1) is made from corrugated cardboard that is folded and may be glued together to form a housing (100). FIGS. 9G and 9H depict a housing (100). Specifically, FIG. 9G depicts the housing (100) as it is being folded into its final form during assembly. FIG. 9H depicts the housing (100) in its final form, wherein the folded cardboard outer sleeve (1) has been glued together or otherwise completed. In other embodiments, as discussed herein, the outer sleeve (1) may be made of any material that provides sufficient insulation, weather resistance, and structure, and the outer sleeve (1) may be bonded using any binder or material known in the art.

In some embodiments, the housing (100) may be a semi-rigid plastic circular housing with internal corrugations promoting regulated oxygen availability to any number of heating elements. In such a case, the housing (100) may include any number of individually packaged heating elements and one (or more) internal plastic tube encasing a highly absorptive and wicking fiber blend. The housing (100) may also include a hollow core.

Any embodiment discussed in this application may include some means for regulating the oxygen flow into the housing (100). For example, some embodiments of the housing (100) include the use of toggle end caps allowing the user to control the amount of molecule dispense. In some embodiments, the toggle end caps on both ends of the housing (100) may be open or closed to any extent to regulate the oxygen flow and molecule dispense. Further, by closing off the oxygen pathways, the chemical reaction may be stopped, along with subsequent molecule dispense. In other embodiments, the housing (100) may be placed into an airtight container, such as a bag made of a plastic barrier film, so as to stop or delay the chemical reaction. In other embodiments, the primary external air intake/exhaust slots (4) or the primary internal air intake/exhaust slots (5) may be obstructed to regulate oxygen flow.

Figure 10A:
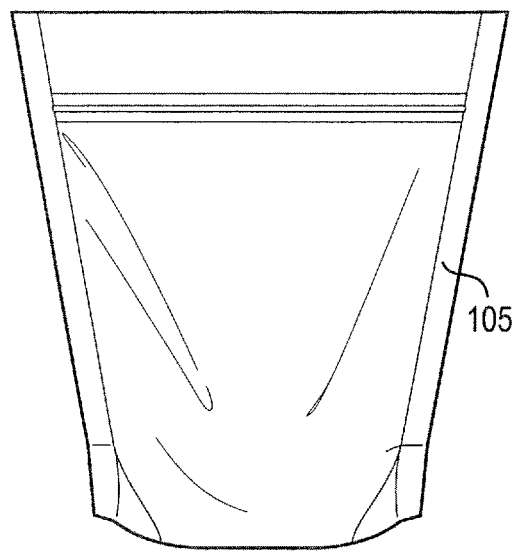
FIGS. 10A-10C depict an embodiment of a molecule dispense system that includes a pouch or bag that may be used to store the housing for periods of time.
Figure 10B:
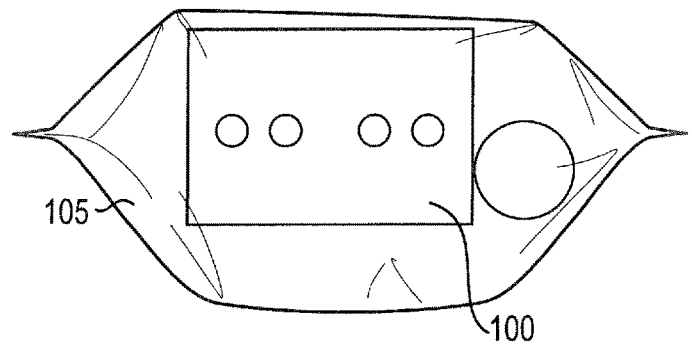
Figure 10C:
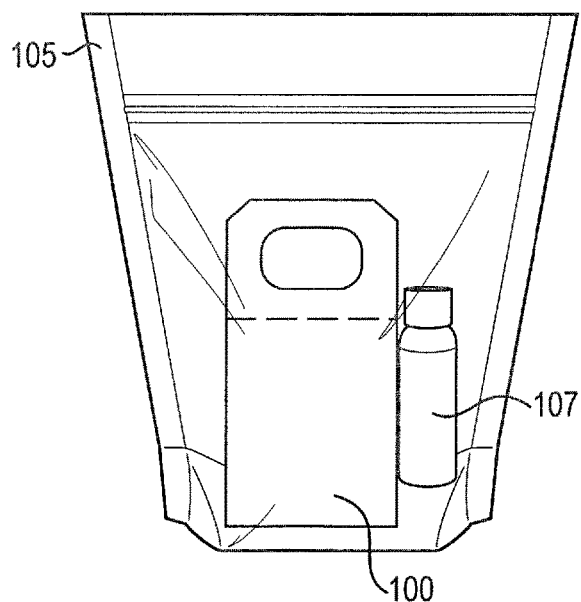

FIGS. 10A-10C depict a pouch or bag (105) that may be used to store the housing (100) for periods of time. For example, the housing (100) may be stored in the pouch or bag (105) after manufacturing until being used by a consumer. The pouch or bag (105) may be comprised of a polymer composite assembly that includes either a metallic film coat or a polymer material that has been impregnated with graphene (or the like). In any case, the pouch or bag (105) will typically be made of a material that is capable of restricting the flow of oxygen through the material itself. The pouch or bag (105) may be used to create an oxygen-free environment to prevent the chemical reactions from occurring in the heating elements (9, 16) during storage. In other embodiments, some other packaging for the heating elements (9, 16) may prevent the chemical reactions from occurring during storage. In the embodiment depicted in FIG. 10C, the pouch or bag (105) may also hold a container of molecules to be dispensed (107). In such an embodiment, a user may pour (or otherwise distribute) molecules from the container (107) into the absorption pads (11, 14) before use. In other embodiments, the absorption pads (11, 14) may include all of the molecules necessary for the system to function.

Figure 11:
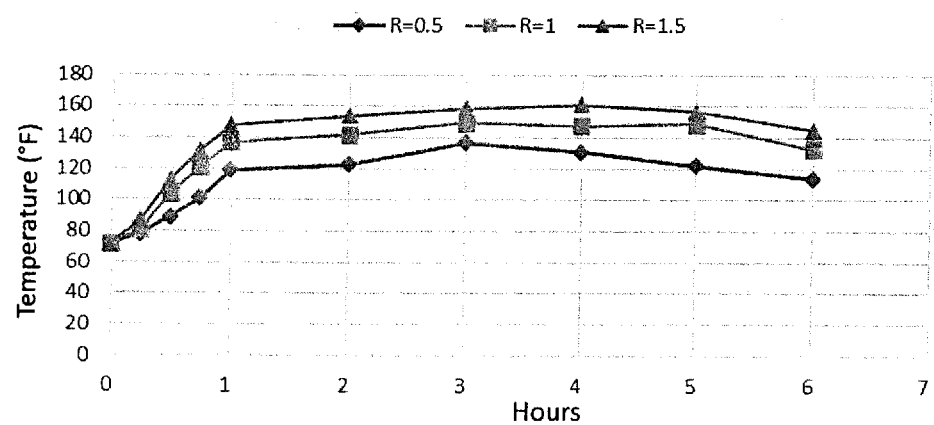
FIG. 11 illustrates the impact housing insulation thickness has on maximum absorption pad temperature as a function of time when an embodiment of the housing is subjected to an ambient environment having a temperature of 72 degrees Fahrenheit.

FIG. 11 illustrates the impact housing (100) insulation thickness has on maximum absorption pad (11) temperature as a function of time when an embodiment of the housing (100) is subjected to an ambient environment having a temperature of 72 degrees Fahrenheit. The level of insulation may be determined by product performance and target retail product cost requirements. For example, the two heating element embodiment depicted in FIG. 1 may utilize multiple layers of B-Flute corrugate material, which may create an overall system R-Value slightly greater than 1. Temperature performance over time is shown via the plot points over a 6-hour period.

Figure 12:
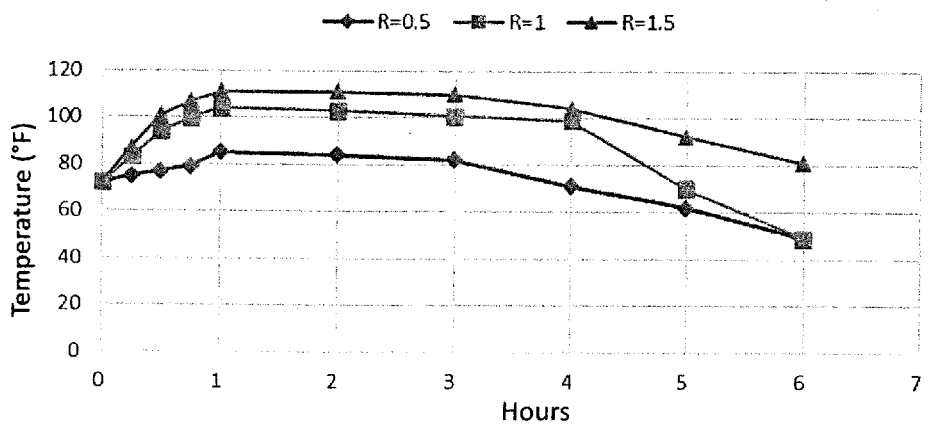
FIG. 12 illustrates the impact housing insulation thickness has on maximum absorption pad temperature as a function of time when an embodiment of the housing is subjected to an ambient environment having a temperature of 3 degrees Fahrenheit.

FIG. 12 illustrates the impact housing (100) insulation thickness has on maximum absorption pad (11) temperature as a function of time when an embodiment of the housing (100) is subjected to an ambient environment having a temperature of 3 degrees Fahrenheit. The level of insulation may be determined by product performance and target retail product cost requirements. For example, the two heating element embodiment depicted in FIG. 1 may utilize multiple layers of B-Flute corrugate, which may create an overall system R-Value slightly greater than 1. Temperature performance over time is shown via the plot points over a 6-hour period. Increasing the housing's (100) R-Value may flatten out the curve over time, possibly increasing absorption pad (11) temperature and run time.

One embodiment of a molecule dispense system in accordance with this application is comprised of an insulated container or housing (100) that may encompass exothermic, and possible additional synergistic or supporting, chemical reactions. The housing (100) may effectively encompasses a molecular core (of, for example, the absorption pads (11, 14)) configured in any configuration. In an embodiment, such a configuration may be a layered, stack-up orientation. In some embodiments, the housing (100) includes a molecular core (like the absorption pads (11, 14)) and chemical reactions that may be effectively shielded from one another through the use of one or more separators (10, 15). The separators (10, 15) may be static with pre-determined dimension and porosity, or dynamic in nature, extending and contracting or opening and closing as a function of the operating environment temperature. In each case, the separators (10, 15) may simultaneously regulate oxygen intake and molecule exhaust through integrated ports or holes over an extended time duration.

The heating elements (9, 16) may focus and drive the non-flammable, odorless heat, created by the exothermic reactions therein. The heating elements (9, 16) may be in direct contact with and oriented perpendicular to the surface of a single (or more) moisture-resistant separator (10, 15). The heat may be focused through a single (or more) absorption pad (11, 14) before exhausting to the ambient environment. The absorption pads (11, 14) in a direct contact, stack-up embodiment may be comprised of a material with a lesser R-Value (i.e., the capacity of an insulating material to resist heat flow) than that of a related housing (100) having a greater R-Value. This R-Value difference may create a useful path of least resistance to heat flow through the absorption pads (11,14) into the ambient environment. The thickness of the absorption pads (11, 14) and material selection may be determined by a required application run time, desired absorption pad operating temperature, and other variables.

The housing (100) generally may be effective to focus and force heat created by the heating elements (9, 16) internal to the housing (100) through a molecular core (which may be a stack-up including the absorption pads (11, 14)) and out to the ambient environment through the primary external air intake/exhaust slots (4). The housing (100) material may be configured to apply reactive, compressive, or other forces upon the internal components (103) of the housing (100) over the life of the reactions. The primary external air intake/exhaust slots (4) may serve to regulate oxygen intake sufficient to feed and sustain the internal chemical reactions, as well as serve as the path of least resistance for propagating heat flow and subsequent molecule dispense. Stated alternately, the housing (100) may be designed to regulate both oxygen intake and energy loss through strategic integration of container geometry, material selection, and heat transfer design principles (including without limitation convection, conduction, and radiation).

Figure 13:
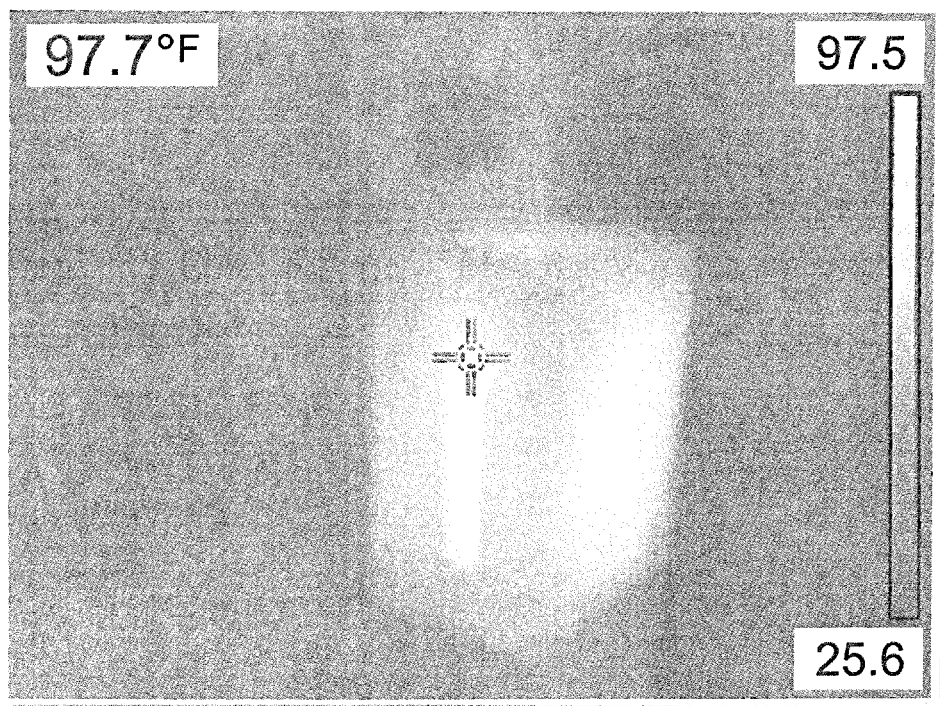
FIG. 13 depicts images from a thermal camera, which images illustrate heat radiating from the primary external air intake/exhaust slots of the housing, and not from the other portions of the housing.
Figure 14:
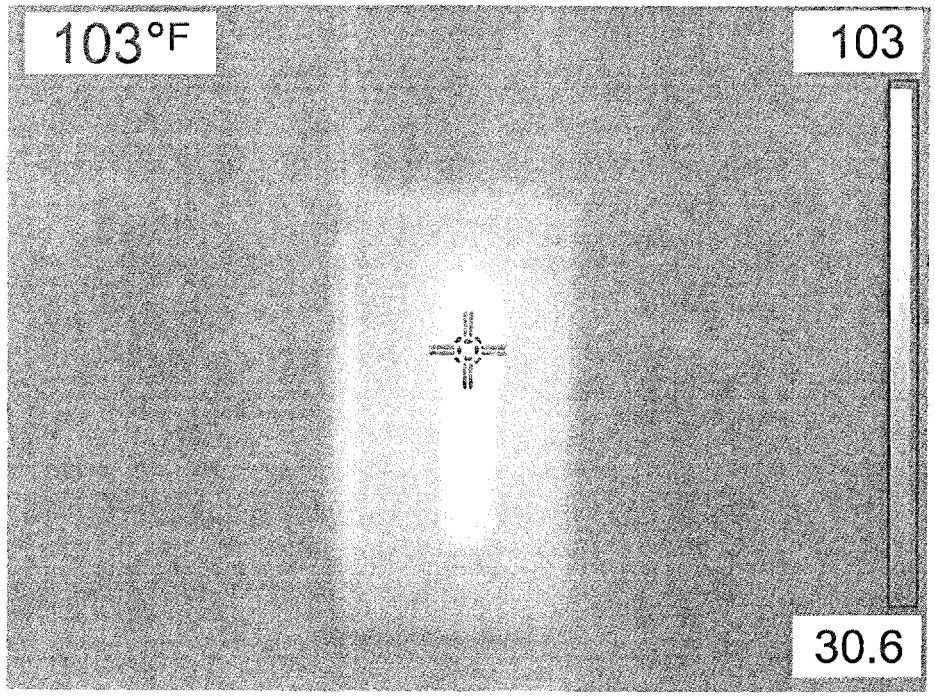
FIG. 14 depicts images from a thermal camera, which images illustrate heat radiating from the primary external air intake/exhaust slots of the housing, and not from the other portions of the housing.

For example, in an embodiment, the housing (100) generally eliminates, or greatly reduces, convention heat loss to the ambient environment through the closed portions of the housing (100). This will generally leave only conduction heat transfer from the heating elements (9, 16) to the absorption pads (11, 14) and relatively minor radiative heat transfer through the housing (100). Convention may then force the molecules to be dispensed out of the housing (100) while drawing in new air and oxygen. For example, FIGS. 13 and 14 show images from a thermal camera, which images illustrate that heat radiates from the primary external air intake/exhaust slots (4) of the housing (100), and not from the other portions of the housing (100). The overall effect of this reduction of convection around the heating elements (9, 16) is to reduce heat loss to the ambient environment and increase heat applied to dispensing molecules from within the housing (100).

Further, convection within the housing (100) is generally controlled and focused by the construction of the internal components (103) and housing (100). For example, a heating cycle based on the embodiment of FIGS. 9A-9H will now be discussed to illustrate how heat moves through the housing (100). As the chemical reactions in the heating elements (9, 16) begin, the housing (100) and the internal components (103) may generally be at ambient temperature, or at least as at the same temperature as each other. In this state, the separators (10, 15) may generally have the tabs (109) that cover the sides of the heating elements (9, 16). These tabs (109), due in part to the compression placed on the internal components (103), may limit the amount of oxygen that is able to reach the heating elements (9, 16) and air that is able to move in through convention in the region of the heating elements (9, 16). This in turn may allow for a controlled startup of the chemical reactions. As the internal components heat up, conduction may heat the absorption pads (11, 14) through the separators (10, 15), as well as any molecules carried by the absorption pads (11, 14). Oxygen may be drawn into the housing (100) via convention as air is heated within the housing (100). This heated air may rise, cool, and fall, while some heated air and molecules may escape through the primary external air intake/exhaust slots (4) of the housing (100).

In some embodiments, as the housing (100) heats up, the internal components (103) may swell and expand. This swelling may increase the efficiency of any heat conduction. Further, the swelling may cause compression in the absorption pads, potentially assisting in movement of the molecules to be dispensed. Further the swelling of the heating elements (9, 16) may cause the separators (10, 15) to reduce the extent of and flatten the bends at the tabs (109). This, in turn, may increase the oxygen flow to the heating elements (9, 16), which may allow for a more consistent reaction as time goes by, at least because the heating elements (9, 16) may require increased oxygen as the reaction reaches a steady-state.

Further, the absorption pads (11, 14) may be oriented to improve the thermal efficiency of the heating process. For example, the absorption pads (11, 14) may be designed so that the sides of the absorption pads (11, 14) oriented towards sides of the housing (100) that do not include the primary external air intake/exhaust slots (4) are compressed against the sides of the housing (100). This compression may create an insulatory seal that prevents convection of heat and molecules in those directions through the absorption pads (11, 14). Similarly, the absorption pads (11, 14) may be designed so that the sides of the absorption pads (11, 14) oriented towards sides of the housing (100) that do include the primary external air intake/exhaust slots (4) are not compressed against the sides of the housing (100). This lack of compression may create a low resistance pathway for the convection of heat and molecules in the direction of the primary external air intake/exhaust slots (4) through the absorption pads (11, 14).

Figure 9A:
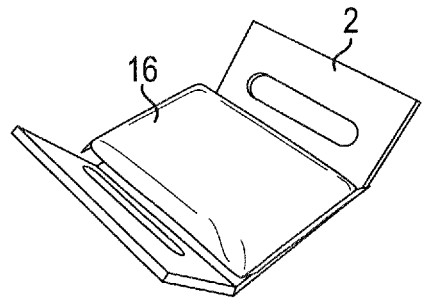
FIGS. 9A-9H depict an embodiment of a housing and related internal components that do not include air scaffolds.
Figure 9B:
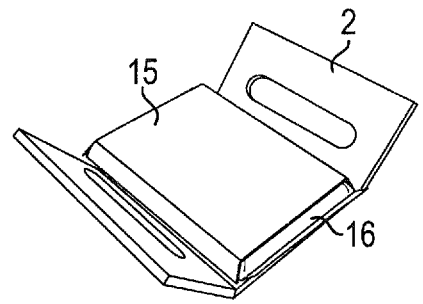
Figure 9C:
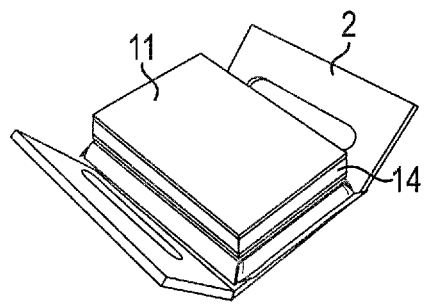
Figure 9D:
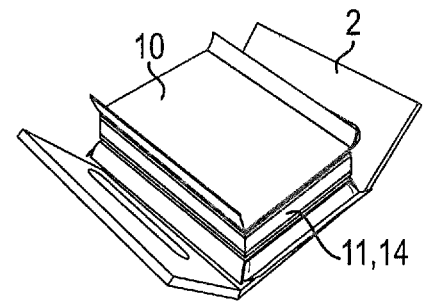
Figure 9E:
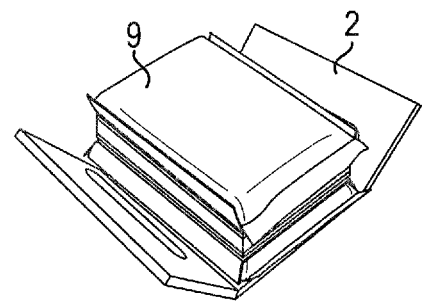
Figure 9F:
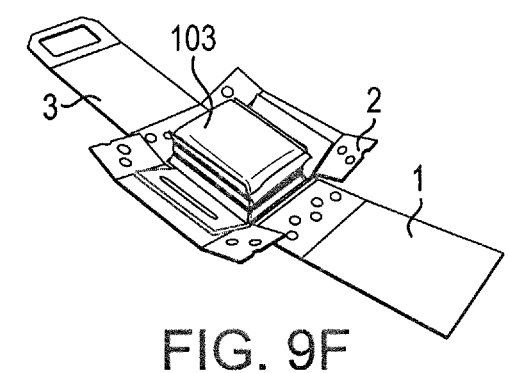
Figure 9G:
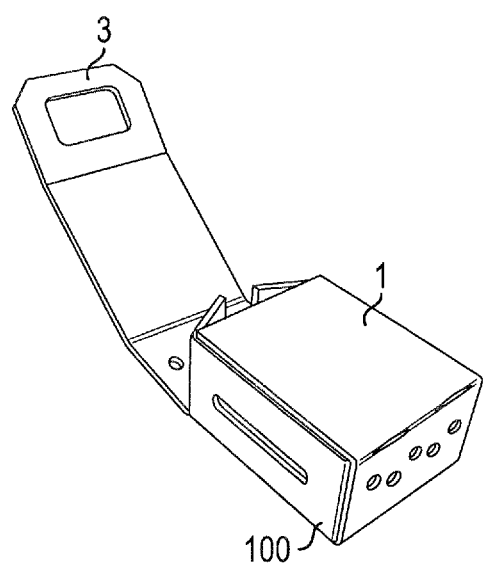
Figure 9H:
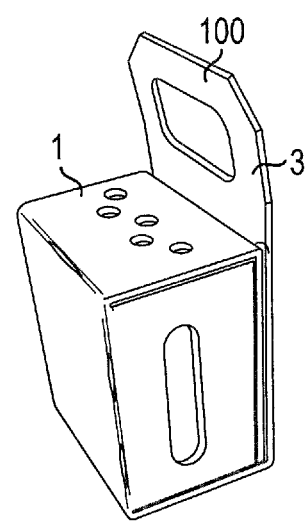

Similarly, as depicted in FIG. 9C and discussed above, the absorption pads (11, 14) may be stapled together. This forms an air gap between the two absorption pads (11, 14). This air gap may facilitate a reduced resistance to heat flow through and around the absorption pads (11, 14) as the chemical reactions begin. This may be beneficial to the startup of the chemical reactions and early molecule dispense. As the internal components (103) heat up, they may swell, as discussed above. This swelling may, in turn, reduce the air gap. This swelling may then increase the resistance of heat flow through the internal components (103), which may increase overall chemical reaction runtime and produce a relatively stable molecule dispense rate over the runtime.

Further, the thermal efficiency of the heating process may be improved by ensuring that large portions of the absorption pads (11, 14) are insulated from the ambient environment. For example, in an embodiment, 75 percent or more of the absorption pads' (11, 14) surface area may be insulated from the ambient environment. In some embodiments, the ratio of insulated surface area of the absorption pads (11, 14) to the exposed surface area of absorption pads (11, 14) may be greater than 4:1. In other embodiments, the ratio of insulated surface area of the absorption pads (11, 14) to the exposed surface area of absorption pads (11, 14) may be greater than 4.6:1. Generally, the lower the ratio of insulated surface area of the absorption pads (11, 14) to the exposed surface area of absorption pads (11, 14), the shorter the runtime in cold environments due to overactive heat loss.

In an embodiment, the housing (100) geometry and internal components' (103) orientation may be configured, stacked, or layered in a compressive contact relationship so as to focus and drive a non-flammable, odorless heat created by the exothermic reaction-based heating elements (9, 16). Such a focus may be perpendicular to the surface of moisture-resistant separators (10, 15), and/or absorption pads (11, 14). This attention to thermal transfer/heat flow may facilitate energy efficient molecule dispense within the absorption pads (11, 14) without electronics, electricity input, or sophisticated controls.

The housing (100) materials may be, but are not limited to, composites or substrates with cost-effective, thermal insulation properties. Materials such as pulp or corrugated cellulose, expanded or extruded polystyrene, polyurethane foams, aerogels, or other cost-effective materials commensurate with the usage application may be used. Inadequate thermal insulation may allow heat to inefficiently escape the housing (100) on all sides, as opposed to being driven through the absorption pads (11, 14). The amount of molecules dispensed may be proportional to the amount of heat being driven through the absorption pads (11, 14). More heat in such a case may lead to more molecules being dispersed, which may result in greater product performance and user experience.

In some embodiments, the relevant exothermic reactions within the housing (100) may generate absorption pad (11, 14) temperatures approaching 180 degrees Fahrenheit without supplementary gas or resistive element-based heating elements, depending upon the internal components (103) and the orientation of the internal components (103). A temperature difference between the absorption pads (11, 14) and the ambient environment may be greater than 60 degrees Fahrenheit when the housing (100) is subjected to an ambient environment between 0 and 100 degrees Fahrenheit. This temperature difference may be sufficient to promote molecule dispense in a sustained, timed-release format.

The housing (100) material's resistance to heat flow (R-Value) is generally proportional to the exothermic reaction's run time, as well as the average and maximum operating temperatures. In many embodiments, the material used to form the housing (100) may be chosen based on the required average run time, core temperature, product cost target, and other variables. Typically, the greater the housing's (100) R-Value, the greater the product cost, run time, and operating temperature. As an example, consumer usage applications, such as deer hunting in Canada in November, where operating temperatures are typically about 20 degrees Fahrenheit, require sufficient housing (100) insulation to drive the chemical reaction heat through the absorption pads (11, 14). On the other hand, deer hunting in Georgia in November may have an ambient environmental operating temperature of about 60 degrees Fahrenheit. Generally, exothermic chemical reactions are able to generate a predetermined quantity of heat. Heat inefficiently escaping through the housing (100) into the environment, due to inadequate insulation material selection, design geometry, or adherence to thermal transfer design principles, may produce less than desirable molecule dispense, which may lead to poor product performance and low user satisfaction.

In some embodiments, the material of the housing (100) may have an R-value greater than 2 per inch at 72 degrees Fahrenheit. Such materials include without limitation corrugated cardboard, EVA foams, and other insulating materials known to persons of ordinary skill in the art. Further, as would be understood by a person of ordinary skill in the art, the R-value of a given material may change based on the thickness of the material, the ambient temperature, and other factors. Further, the material for the housing (100) may be a compound of different materials which have R-Values that together add to being equal to or greater than 2.

In addition to facilitating molecule dispense, the housing (100) may also serve as a user interface, allowing the user to sit, throw, drag, or hang the housing (100), largely independent of weather conditions such as rain, snow, sleet, or shine. Material selection for the housing (100) may affect overall product performance, for example, product durability, cost, and aesthetic value, amongst other variables.

The housing (100) may be configured in many different form factors. For example, the housing may have generally rectangular, triangular, square, circular, or any other-shaped cross-sections. The housing (100) may include one, or a plurality of heating elements (9, 16). For example, in some embodiments, the housing (100) may include between 2 and 4 heating elements. The number of heating elements (9, 16) included in the housing (100) may depend on the housing's (100) form factor, resultant geometry, application requirements, or other variable. The housing (100) may serve as a primary barrier to heat flow, encompassing and forcing the heat created by the chemical reactions through the absorption pads (1, 14) and out to the atmosphere through the primary external air intake/exhaust slots (4).

Multiple chemical reactions, exothermic or otherwise, may be integrated into the housing (100). The chemical reactions, which are typically exothermic, generally occur within the heating elements (9, 16). The chemical reactions may be capable of producing odorless heat of sufficient quantity to dislodge molecules and propel the molecules into the ambient environment. Each chemical reaction may be self-contained in a packaging. Such packaging may be a flexible, porous cloth pouch or other oxygen-regulated containment material. The packaging will typically be sufficiently porous, via perforation or other oxygen-inducing format, proportional to the oxygen availability of the usage environment, run time, average temperature requirement, maximum temperature requirement, or other variable. For example, heavily insulated housings (100) operating in a cold usage application will require chemical reaction packaging materials with a higher porosity than those operating in hot environments with slightly insulated housings (100). In some embodiments, the housing (100) may include chemical reactions capable of producing oxygen as a by-product, which may support and sustain exothermic, oxygen-based reactions. As water vapor generally decreases exothermic reaction runtime and average temperature generation, in some embodiments, chemical reactants, desiccant materials, or other materials capable of converting or absorbing water vapor may be used to support and sustain exothermic, oxygen-based reactions.

Over the life of the chemical reactions, which is typically between 1 to 12 hours, the heating elements may swell in cross-section and thereby exert compressive forces on the housing (100) and the molecule-saturated absorption pads (11, 14). These mechanical compressive forces may work in concert with the focused heat flow internal to the housing (100), which may increase molecule dispense over time by effectively "squeezing" the molecular core, which may promote increased dispense efficiency.

Further, in an embodiment, the system is configured to be capable of producing and sustaining an absorption pad temperature a minimum of 30 degrees Fahrenheit higher than the operating environment temperature for greater than 3 hours. In some embodiments, the system is configured to be capable of producing heat for more than 4 hours. In other embodiments, the system is configured to be capable of producing heat for more than 5 hours. In yet other embodiments, the system is configured to be capable of producing heat for more than 6 hours. In yet other embodiments, the system is configured to be capable of producing heat for more than 7 hours. In yet other embodiments, the system is configured to be capable of producing heat for more than 8 hours. In any of these embodiments, the system is configured to be capable of producing and sustaining an absorption pad temperature a minimum of 20 degrees Fahrenheit higher. In other embodiments, the system is configured to be capable of producing and sustaining an absorption pad temperature a minimum of 25 degrees Fahrenheit higher. In yet other embodiments, the system is configured to be capable of producing and sustaining an absorption pad temperature a minimum of 35 degrees Fahrenheit higher. In yet other embodiments, the system is configured to be capable of producing and sustaining an absorption pad temperature a minimum of 45 degrees Fahrenheit higher.

The chemical-driven, exothermic heating elements (9, 16), which may be pads, pouches, or other forms, may, in some embodiments, employ a one-time exothermic chemical reaction. One type of heating element, which may frequently be used for hand warmers, is triggered by exposing the heating element containing slightly moist iron powder and salt or catalysts to oxygen, which iron powder rusts over a period of hours after being exposed to oxygen. An example of the results of such exothermic reactions utilizing specific embodiments of the system (100) as described herein are depicted in FIGS. 11-14. Another type of heating element contains separate compartments within a pad. When a user squeezes the pad, a barrier ruptures and the compartments mix, producing heat. In either case, the heating elements may be covered by a fabric barrier to, in part, hold in the heating element contents including, for example, the iron powder. This fabric barrier may resist the flow of oxygen into the chemical reaction. Accordingly, in some embodiments, holes may be made in the fabric barrier to facilitate increased oxygen flow to the chemical reaction.

The heating elements (9, 16) may be packaged in an oxygen-free environment prior to use. For example, the housing (100) and the heating elements (9, 16) may be packaged in an air-tight product packaging with no air or oxygen internal to the product packaging. Initiating the desired chemical reactions may then require a user to pierce or manipulate the product packaging sufficiently to expose the housing (100) or heating elements (9, 16) to an oxygen atmosphere. In an embodiment, the chemical reactions may be initiated by tearing open the product packaging, which may be fitted with a shear-based film. The shear-based film may cover perforated membrane holes on the heating element packaging, which may effectively shield the heating elements (9, 16) from oxygen exposure. Upon removal of the shear-based film, the perforated holes will be uncovered, allowing oxygen to initiated the desired chemical reactions. Alternately, the heating elements (9, 16) may be placed into a prepackaged assembly where user removal of an exterior packaging immediately initiates the chemical reactions. For example, in an embodiment, a three-layered pouch having a pair of heating elements (9, 16) surrounding pre-saturated absorption pads (11, 14) may be prepackaged into an airtight exterior packaging having no air therein. This type of integration, or cartridge format, would frequently be inserted into a durable, reusable housing (100), as opposed to a disposable, one-time housing (100).

In another embodiment, each heating element (9, 16) may have its own shear-based film packaging. To initiate the chemical reactions, a user may be required to tear or otherwise open one or more individual shear-based film packages to expose the heating element (9, 16) to oxygen. In such an embodiment, the shear-based film may further serve as a separator between each heating element (9, 16) and a respective side of a relevant absorption pads (11, 14), potentially obviating any need for additional separators (10, 15).

The internal components (103) contained within the housing (100) may be oriented in a stack-up, rolled, or other configuration such that each internal component (103) is in direct contact with components on either side. For example, the internal components (103) may be arranged in a stack-up orientation with the absorption pads (11, 14) encompassed (directly or with intervening layers) by separators (10, 15), which are then encompassed by the heating elements (9, 16). All of these layers may then be encased within the housing (100). Other embodiments may also have a stack-up orientation wherein the heating elements (9, 16) are encompassed by, for example, the separators (10, 15). The separators (10, 15) may then be encompassed by the absorption pads (11, 14), and all of these components may be encased within the housing (100). In some embodiments, there may be intervening materials preventing direct contact between some or all of the individual components.

The separators (10, 15) may be, without limitation, moisture resistant and poly-faced cardboard or plastic films. The separators (10, 15) may extend and/or contract, or if perforated, may open and/or close as a function of operating temperature. Stated differently, the separators (10, 15) may be a polymer or other material with an inherent negative or positive temperature coefficient or a shape memory polymer or alloy or similar material. In other, typically low-cost embodiments, the separators (10, 15) may be fabricated from cellulose or polymer substrates incorporating a hydrophobic film or coating. The separators (10, 15) may be, without limitation, formed into configurations including mechanical separating geometry designed to protect the chemical reactions from moisture degradation, for example, from liquid application onto the absorption pads (11, 16) or during molecule dispense or condensation accumulation.

As with the heating elements (9, 16) described above, the absorption pads (11, 14) may also be designed to swell or expand as molecules are added and contract has heat energy intensity increases. Such expansion and contraction may promoting increased molecule dispense efficiency. The expansion of the absorption pads (11, 14) may increase total molecule holding capacity while generating compressive forces against the housing's (100) framework. These internal reactionary forces, working in conjunction with heat energy, may efficiently and effectively "squeeze" the molecules to be dispensed, possibly resulting in an efficient dispense of the molecules into the ambient environment. The absorption pads (11, 14) may be oriented in a flat configuration, which may lead to molecule dispense across the open surface area, or rolled up, similar to a cigarette, which may lead to molecule dispense across the circular ends and/or balance of exposed surfaces. In other embodiments, the absorption pads (11, 14) may be any shape or size and have any orientation. Further, it is noted that generally, molecule dispense is proportional to the percentage of exposed surface area of the absorption pads (11, 14).

In an embodiment of the system designed for applications in an ambient environment with a temperature above 32 degrees Fahrenheit, it may be beneficial to increase the percentage of exposed surface area through the use of air scaffolds (12, 13). The air scaffolds (12, 13) may provide an air gap between multiple absorption pads (11, 14) so as to increase absorption pad (11, 14) surface area exposure to the ambient environment, which will typically facilitate increased molecule dispense.

In any case, the housing may be made to have any shape, size, and/or function. Most embodiments of the housing (100) will be either a disposable or a durable good. Generally, disposable consumer products may require the absorption pads (11, 14) to be loaded with molecules for dispensing immediately prior to use. Generally, durable consumer products may include consumable cartridges, which may include absorption pads (11, 14) that are pre-saturated prior to packaging, allowing a user to open a pre-dosed package prior to use, generally limiting a likelihood of molecule spillage and skin exposure to the molecules. In some embodiments, the absorption pads (11, 14) may be packaged in a material that may resist molecule dispensing until being opened. In some embodiments, this packaging may be used with, or to serve as, the separators (10, 15). In some such embodiments, the packaging for the absorption pads (11, 14) may be a film with removable ends. In such embodiments, the ends may be removed when the system is intended to be used. In this case, the open ends of the packaging will allow movement of molecules, generally due to convention, out of the absorption pads (11, 14). Further, the remaining portions of the packaging may reduce moisture introduction to the heating pads (9, 16) and facilitate conductive heating of the absorption pads (11, 14) and the molecules therein.

While the invention has been disclosed in conjunction with a description of certain embodiments, the detailed description is intended to be illustrative and should not be understood to limit the scope of the present disclosure. As would be understood by one of ordinary skill in the art, embodiments other than those described in detail herein are encompassed by the disclosed invention. Modifications and variations of the described embodiments may be made without departing from the spirit and scope of the invention.

It will further be understood that any of the ranges, values, properties, or characteristics given for any single component of the present disclosure can be used interchangeably with any ranges, values, properties, or characteristics given for any of the other components of the disclosure, where compatible, to form an embodiment having defined values for each of the components, as given herein throughout. Further, ranges provided for a genus or a category can also be applied to species within the genus or members of the category unless otherwise noted.

Finally, the qualifier "generally," and similar qualifiers as used in the present case, would be understood by one of ordinary skill in the art to accommodate recognizable attempts to conform a device to the qualified term, which may nevertheless fall short of doing so. This is because terms such as "circular" are purely geometric constructs and no real-world component is a true "circular" in the geometric sense. Variations from geometric and mathematical descriptions are unavoidable due to, among other things, manufacturing tolerances resulting in shape variations, defects and imperfections, non-uniform thermal expansion, and natural wear. Moreover, there exists for every object a level of magnification at which geometric and mathematical descriptors fail due to the nature of matter. One of ordinary skill would thus understand the term "generally" and relationships contemplated herein regardless of the inclusion of such qualifiers to include a range of variations from the literal geometric meaning of the term in view of these and other considerations.

The invention claimed is:

1. A system for dispensing molecules, comprising:
a housing;
a molecule holding pad internal to said housing;
a first chemical reaction heat source internal to said housing;
a second chemical reaction heat source internal to said housing;
a first flexible separator internal to said housing; and
a second flexible separator internal to said housing,
wherein said first chemical heat source is in contact with said first flexible separator;
wherein said first flexible separator is in contact with said molecule holding pad;
wherein said molecule holding pad is in contact with said second flexible separator;
wherein said second flexible separator is in contact with said second chemical reaction heat source; and
wherein at least one of said first chemical reaction heat source and said second chemical reaction heat source is reactive to oxygen.

2. The system of claim 1, wherein said system is configured to produce heat from said first chemical reaction heat source and from said second chemical reaction heat source for over 6 hours.

3. The system of claim 1, wherein at least one of said first chemical reaction heat source and said second chemical reaction heat source contains iron.

4. The system of claim 1, wherein said housing directs heat from said first chemical reaction heat source and said second chemical reaction heat source to said molecule holding pad.

5. The system of claim 1, further comprising another molecule holding pad arranged adjacent to said molecule holding pad and between said first chemical reaction heat source and said second chemical reaction heat source.

6. The system of claim 5, wherein said system is configured to be capable of sustaining a temperature of each of said molecule holding pad and said another molecule holding pad at a minimum of 30 degrees Fahrenheit higher than an operating environment temperature for greater than 3 hours.

7. The system of claim 5, wherein said molecule holding pad is attached to said another molecule holding pad.

8. The system of claim 1, wherein said first flexible separator and said second flexible separator are moisture barriers.

9. The system of claim 8, wherein said first flexible separator and said second flexible separator are configured to regulate oxygen flow to said first chemical reaction heat source and said second chemical reaction heat source, respectively.

10. The system of claim 8, wherein said first flexible separator and said second flexible separator are configured to increase oxygen flow to said first chemical reaction heat source and said second chemical reaction heat source, respectively, as a temperature of each of the first chemical reaction heat source and said second chemical reaction rises.

11. The system of claim 1, wherein said housing is enclosed with a bag that inhibits oxygen from entering said housing.

12. The system of claim 11, further comprising a molecule dispensing container including scent molecules in said bag.

13. The system of claim 1, wherein said housing comprises a material having an R-value greater than 2 per inch at 72 degrees Fahrenheit.

14. The system of claim 1, wherein said molecule holding pad is configured to expand when heated.

15. A system for dispensing molecules, comprising:
a housing;
a molecule holding pad internal to said housing;
a first chemical reaction heat source internal to said housing; and
a first flexible first separator internal to said housing and positioned between said molecule holding pad and said first chemical reaction heat source,
wherein said first chemical reaction heat source is reactive to oxygen, and
wherein said housing has sufficient rigidity to hold said molecule holding pad under compression before when said first chemical reaction heat source actively produces heat.

* * * * *